(12) United States Patent
Börner et al.

(10) Patent No.: US 8,223,924 B2
(45) Date of Patent: Jul. 17, 2012

(54) GRATING WITH A LARGE ASPECT RATIO, IN PARTICULAR TO BE USED AS AN X-RAY OPTICAL GRATING IN A CT SYSTEM, PRODUCED BY A LITHOGRAPHY METHOD

(75) Inventors: Martin Börner, Stutensee (DE); Eckhard Hempel, Fürth (DE); Hartmut Kumm, Karlsruhe (DE); Jürgen Mohr, Sulzfeld (DE); Elena Reznikova, Linkenheim-Hochstetten (DE)

(73) Assignees: Siemens Aktiengesellschaft, Munich (DE); Karlsruher Institut for Technologie, Karlsruhe (DE)

( * ) Notice: Subject to any disclaimer, the term of this patent is extended or adjusted under 35 U.S.C. 154(b) by 259 days.

(21) Appl. No.: 12/768,052

(22) Filed: Apr. 27, 2010

(65) Prior Publication Data

US 2010/0278297 A1  Nov. 4, 2010

(30) Foreign Application Priority Data

Apr. 30, 2009  (DE) .......................... 10 2009 019 595

(51) Int. Cl.
*G21K 1/00*  (2006.01)
(52) U.S. Cl. .......................... 378/145; 378/16
(58) Field of Classification Search ................ 378/4–20, 378/84–85, 62, 34–35, 145–146; 359/566–576
See application file for complete search history.

(56) References Cited

U.S. PATENT DOCUMENTS

| | | | | |
|---|---|---|---|---|
| 5,812,629 | A * | 9/1998 | Clauser | 378/62 |
| 2007/0183579 | A1 * | 8/2007 | Baumann et al. | 378/145 |
| 2011/0194673 | A1 * | 8/2011 | Teshima et al. | 378/62 |

FOREIGN PATENT DOCUMENTS

| | | |
|---|---|---|
| DE | 102006037281 A1 | 8/2007 |
| DE | 102008049200 A1 | 4/2010 |

OTHER PUBLICATIONS

F. Pfeiffer et al.; Phase retrieval and differential phase-contrast Imaging with low-brilliance X-ray sources; Nature Physics 265, 2006, published online Mar. 26, 2006; Nature Publishing Group; 265, pp. 1-4; Magazine; 2006.

(Continued)

*Primary Examiner* — Hoon Song
(74) *Attorney, Agent, or Firm* — Harness, Dickey & Pierce, P.L.C.

(57) ABSTRACT

A grating with a large aspect ratio is disclosed, in particular to be used as an X-ray optical grating in a CT system and in particular produced by a lithography method. In at least one embodiment, the grating includes a multiplicity of recurring alternating grating webs and grating gaps with a height, and a multiplicity of filler beams, respectively arranged in the grating gaps with a spacing from one another in the direction of the gaps, which beams connect respectively adjacent grating webs over their height. In at least one embodiment, the grating webs and the grating gaps run from a first to a second side of the grating, and a filler beam has a width in the direction of the gaps and this width is at most 10% of the spacing between two adjacent filler beams. In at least one embodiment, the spacings between respective adjacent filler beams in a grating gap do not vary by more than 10% in the entire grating. At least one embodiment of the invention furthermore relates to a CT system containing at least one grating according to at least one embodiment of the invention.

19 Claims, 3 Drawing Sheets

OTHER PUBLICATIONS

Elena Reznikova et al., "Soft X-ray lithography of high aspect ratio SU8 submicron structures", Microsystem Technologies, vol. 14, Nos. 9-11, Oct. 2008, pp. 1683-1688 (6); Others; 2008.

Elena Reznikova et al., "Fabrication of high aspect ratio submicron gratings by soft X-ray SU-8 lithography", Micro Syst. Techn. (2008); Others.

* cited by examiner

A

Detail A

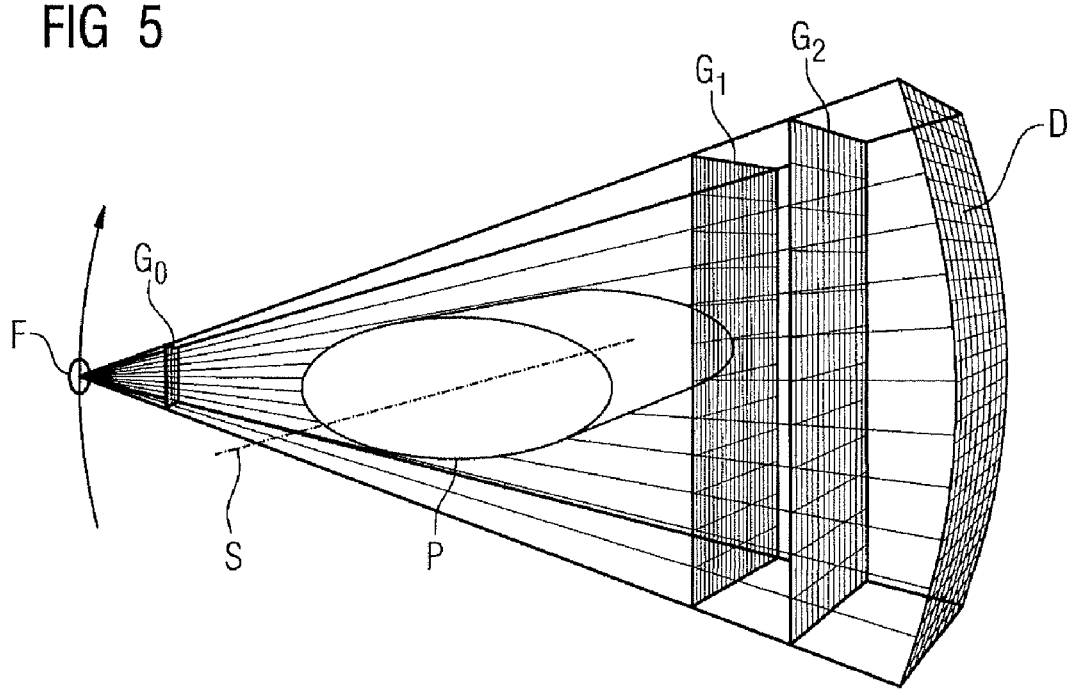

GRATING WITH A LARGE ASPECT RATIO, IN PARTICULAR TO BE USED AS AN X-RAY OPTICAL GRATING IN A CT SYSTEM, PRODUCED BY A LITHOGRAPHY METHOD

PRIORITY STATEMENT

The present application hereby claims priority under 35 U.S.C. §119 on German patent application number DE 10 2009 019 595.5 filed Apr. 30, 2009, the entire contents of which are hereby incorporated herein by reference.

FIELD

At least one embodiment of the invention generally relates to a grating with a large aspect ratio. In particular, at least one embodiment of the invention relates to a grating with a large aspect ratio to be used as an X-ray optical grating in a CT system, produced by a lithography method, having a multiplicity of recurring alternating grating webs and grating gaps with a height, and a multiplicity of filler beams, respectively arranged in the grating gaps with a spacing from one another in the direction of the gaps, which beams connect respectively adjacent grating webs over their height, wherein the grating webs and the grating gaps run from a first to a second side of the grating, and a filler beam has a width in the direction of the gaps and this width is at most 10% of the spacing between two adjacent filler beams.

BACKGROUND

Gratings with a large aspect ratio, that is to say a large ratio between the structure height and the width of the grating gaps, are known. Herein, a large aspect ratio is understood to mean a value greater than 10. However, it should be noted that gratings with an aspect ratio of up to 50 are also known. Given a prescribed grating width, a large aspect ratio requires, in particular, a large structure height, that is to say grating gaps that are as deep as possible. Such gratings are used in e.g. phase-contrast X-ray imaging for determining the phase-shift of an X-ray beam as it passes through an examination object.

Such gratings are usually produced by way of a lithography method, in particular by means of the so-called LIGA method. This method is particularly suitable for producing gratings with large structure heights—up to 3 mm—and the smallest possible lateral dimensions—up to 0.2 μm. This allows the realization of large aspect ratios. Herein, a radiation-sensitive layer, the resist, is illuminated using the shadow cast by a working mask, as a result of which an exact image of the working mask is transferred into the resist. This primary structure represents an exact negative impression of the subsequent grating. Subsequently, the irradiated regions are removed by chemical means. By way of example, a plastic such as PMMA or a negative resist such as SU-8 can be used as a resist. During the irradiation by energetic and parallel X-ray radiation in particular, very high structures with almost perpendicular and very smooth sidewalls can be produced compared to irradiation by UV radiation, and this is useful for the required high aspect ratio.

If these primary structures are generated on a metallic start layer, the structures exposed after the development process can be filled by means of electroplating with different metals or alloys forming the actual grating. After the growth of the grating material, the primary structure is removed and merely the grating structures remain. If the grating material is grown significantly over the structure height of the resist, an interconnected, stable plate is obtained—the grating base—and it supports the grating structures. Overall, a multiplicity of different metals, alloys, ceramics and plastics can be used as grating materials in this method.

The publication "Phase retrieval and differential phase-contrast imaging with low-brilliance X-ray sources" by F. Pfeiffer et al., in Nature Physics (2006) advanced online publication, describes the options for phase-contrast X-ray imaging using an incoherent X-ray source. In order to implement these imaging systems, the production of grating structures with a recurrence in the region of 2 μm and structure heights of at least 100 μm is necessary. These requirements in respect of the height of the absorbing grating structures and the mechanical stability thereof currently present large production-technical problems.

The publication "Fabrication of, high aspect ratio submicron gratings by soft X-ray SU-8 lithography" by E. Reznikova et al., in Micro. Syst. Techn. (2008), describes a method by means of which gratings can be produced with an aspect ratio of greater than 50. Here, the production of virtually defect-free grating structures with a width of up to 1.2 μm and a height of 60 μm was demonstrated. Here, the grating structures consist of the recurring alternating grating webs and grating gaps, wherein a plurality of filler beams are respectively arranged in the grating gaps in order to stabilize the grating webs. Here, the spacing between adjacent filler beams in a grating gap is irregular. This stabilization by the filler beams is required particularly in the high grating structures required for using the gratings in phase-contrast X-ray imaging because the influence of the surface effects, i.e. the capillary forces, acting in the grating gaps to the left and right of a grating web increase strongly as the height increases.

However, this article also describes that structure heights of more than 60 μm lead to bending of the grating webs. As a result of the irregular spacings between the filler beams, capillary forces of different strengths act in the grating gaps. This non-equilibrium of forces leads to a bending of the grating webs between two filler beams. Accordingly, this bending then limits the aspect ratio and such mechanically unstable or bent gratings cannot simply be used in phase-contrast examinations.

SUMMARY

At least one embodiment of the invention improves the grating for the absorption of X-ray radiation known per se further such that it can also be produced with a high aspect ratio or large structure heights in a mechanically stable fashion, for example in order to be suitable for use in phase-contrast X-ray imaging.

The inventors have recognized that the influence of the capillary forces acting in the grating gaps on the adjacent grating webs is dependent on the spacing between two filler beams. Here, a large spacing means a strong influence of the capillary forces due to reducing mechanical stability and a small spacing correspondingly means a weaker influence of the capillary forces. Accordingly, uniform spacing of the filler beams allows a force equilibrium to be set up on both sides of the grating webs and so the capillary forces to the left and the right of a grating web cancel one another. It follows that this can avoid bending of the grating webs up to a certain spacing of the filler beams depending on the width and height of the grating webs.

In this respect, it is possible to select the spacing as a function of the height of the grating structures and the recurrence of the grating when the grating beams have the same spacing. Structures designed in this fashion can realize the desired gratings for phase-contrast X-ray imaging. However, within the scope of procedural accuracies, the spacings between the filler beams considered equal can vary by up to 2 µm. In the case of a very accurate production method, these tolerances can also lie below 0.5 µm.

In order to prevent a second transverse grating from being formed in the case of uniformly spaced filler beams due to the arrangement of the filler beams in the perpendicular direction to the grating webs, the arrangement of the filler beams in each grating gap can be random, with the spacing condition naturally still having to be satisfied.

In order to avoid undesired absorption of the X-ray radiation in the filler beams that is too high, the width of the latter is limited in the direction of the gaps. 3 µm is a recommended value for this.

According to this basic idea, in at least one embodiment of the invention the inventors propose to improve a grating with a large aspect ratio, in particular to be used as an X-ray optical grating in a CT system, produced by a lithography method, having a multiplicity of recurring alternating grating webs and grating gaps with a height, and a multiplicity of filler beams, respectively arranged in the grating gaps with a spacing from one another in the direction of the gaps, which beams connect respectively adjacent grating webs over their height, wherein the grating webs and the grating gaps run from a first to a second side of the grating, and a filler beam has a width in the direction of the gaps and this width is at most 10% of the spacing between two adjacent filler beams, to the effect that the spacings between respective adjacent filler beams in a grating gap do not vary by more than 10% in the entire grating.

Advantageously, the spacings between the respective adjacent filler beams in a grating gap are the same in the entire grating, with this lying within the scope of procedural accuracy. Depending on the accuracy of the production process, the spacings can vary between 0.5 µm and 2 µm.

According to an advantageous embodiment of the grating according to the invention, the spacing between two filler beams arranged adjacently in a grating gap can be selected as a function of the height of the grating webs and grating gaps and the recurrence of the grating. This is represented by the following geometric condition:

$$l = \frac{k}{h} \cdot \left(\frac{p}{2}\right)^3,$$

where l [µm] characterizes the spacing between the filler beams, h [µm] characterizes the height of the grating webs and grating gaps, p [µm] characterizes the recurrence of the grating and k characterizes a constant. This constant k can preferably be less than 5000 µm$^{-1}$, and more preferably lie between 750 µm$^{-1}$ and 2500 µm$^{-1}$.

In a further advantageous embodiment of the grating according to the invention, the filler beams can be positioned randomly in a grating gap, maintaining the spacing condition in each case, in order to avoid a second grating forming across the grating webs. In the process, in each grating gap there is a first filler beam adjacent to the first side of the grating, wherein this first filler beam has a certain spacing from the first side of the grating. Advantageously, this spacing varies within a determined interval for each grating gap. This interval can be selected as a function of the spacing between two adjacent filler beams. In the process, $$(l-5 \text{ µm}) \geq x \geq 5 \text{ µm}$$

holds true, where l is the spacing between two adjacent filler beams and x is the spacing of the first filler beam from the first side of the grating.

The width of a filler beam, that is to say the extent thereof in the direction of the gaps, can preferably furthermore be limited in order to limit the absorption of the X-ray radiation in the filler beams and thus maintain the effectiveness of the grating. In doing so, an upper limit of 3 µm was found to be expedient for the width of the filler beams.

A further advantageous embodiment of the filler beams in the grating according to the invention provides for respectively the first and the last filler beam, that is to say the outer filler beams, to be extended in a grating gap to the extent that they completely fill the distance to the edge of the grating if the latter is smaller than a predetermined value, wherein this value lies between 5 and 10 µm. Since a negative impression is created first during the production of the grating, the provision of the above can prevent the generation of very delicate negative shapes at the edges, which shapes are unstable and can bend very easily.

In the production of the grating according to at least one embodiment of the invention, a primary structure is generated first with the aid of a lithography method and the grating is produced subsequently as a negative impression of this primary structure. The lithography method is preferably an X-ray lithography method. These methods are particularly well suited to the production of gratings with large aspect ratios and grating structures, which are as fine and as deep as possible and are necessary for the use of such gratings in phase-contrast X-ray imaging.

Furthermore, the actual grating can be produced by electrodeposition of the grating material in the primary structure, wherein the primary structure is advantageously formed from a negative resist, in particular SU-8.

Additionally, the grating can be arranged on a grating base during the production, which base is created for example by electroplating the primary structure with the grating material or a different material and it stabilizes the grating structures. As an alternative, the grating can also be arranged on a foil after the production for stabilization purposes.

Moreover, at least one embodiment of the invention relates to a CT system having at least one grating, which is designed as per the features described above.

BRIEF DESCRIPTION OF THE DRAWINGS

In the following text, the invention is described in more detail on the basis of example embodiments with the aid of the figures, with only features required for the understanding of the embodiments of the invention being illustrated. Here, the following reference signs are used: 1: grating web; 2: grating gap; 3: grating base; 4: filler beam; 4.1: region of the first filler beams; 4.2: extended filler beam; b: width of a grating gap; D: detector; F: focus; f: width of a filler beam; h: height of the grating webs; $G_0$: source grating; $G_1$: phase grating; $G_2$: analysis grating; l: uniform spacing between two filler beams; $l_x$: irregular spacing between two filler beams; P: patient; S: system axis; x: spacing between the first filler beam and the first side of the grating.

In detail:

FIG. 5 shows a schematic 3D illustration of a focus/detector system with three gratings.

DETAILED DESCRIPTION OF THE EXAMPLE EMBODIMENTS

Figure 1:
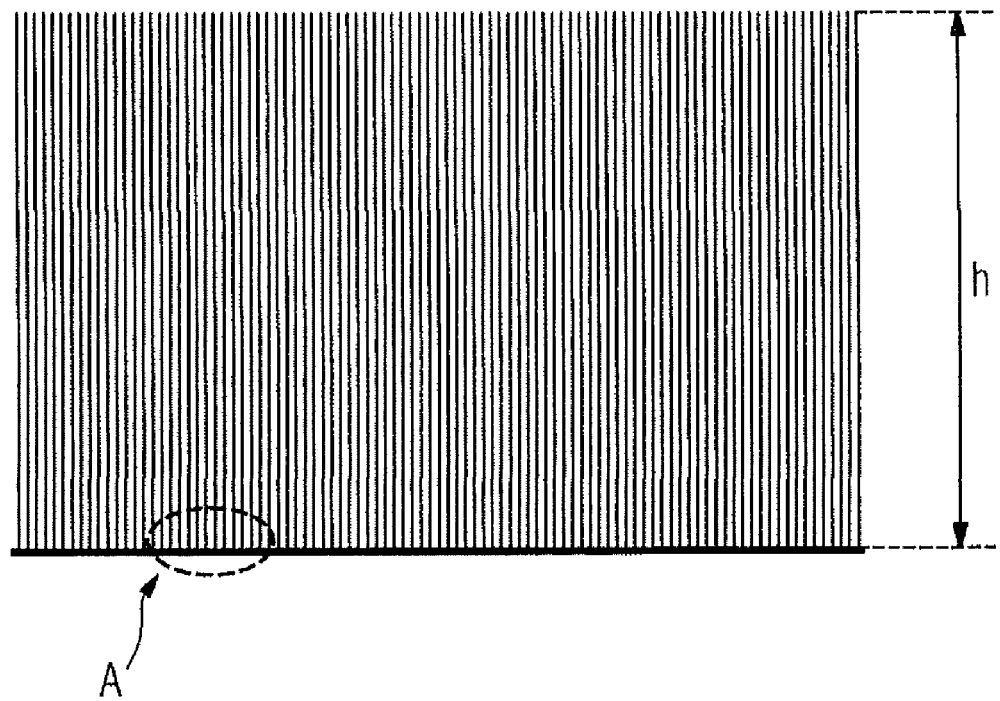
FIG. 1 shows a side view of a grating with a large aspect ratio and a detail A.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

Figure 2:
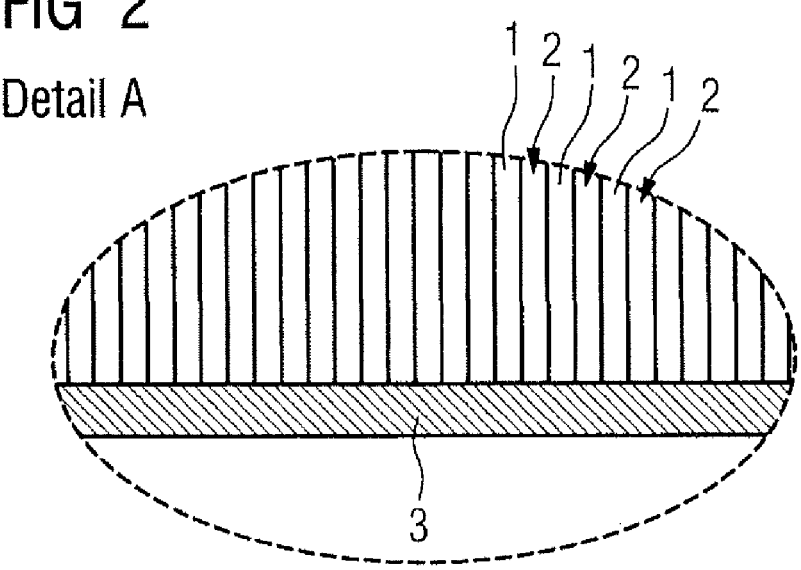
FIG. 2 shows a detail A from FIG. 1.

FIG. 1 shows the side view of a grating with a large height-to-width aspect ratio. Thus, the height h of the grating webs is significantly greater than the width of a grating gap. The recurringly arranged grating webs 1 and grating gaps 2 are interconnected by a grating base 3. This can be seen in the much-enlarged detail A in FIG. 2. Here, the grating base 3 consists of a different material than the grating webs 1.

Figure 3:
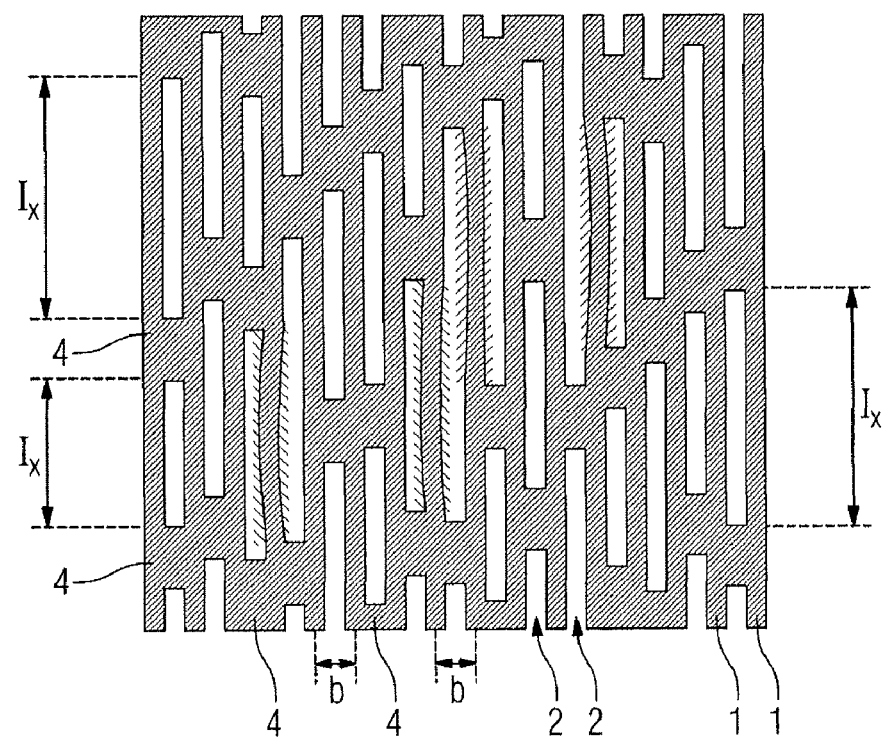
FIG. 3 shows a plan view of a grating with filler beams and a plurality of bends in the grating webs.

FIG. 3 shows a much-enlarged section of a plan view on a grating as per FIG. 1 with the already known arrangement of filler beams 4 in the grating gaps 2. Herein, there are a plurality of filler beams 4 in each grating gap 2, which beams have an irregular spacing $l_x$ between one another. The filler beams 4 connect adjacent grating webs 1 respectively over their entire height. The surface effects are very predominant in the grating gaps 2 due to the very narrow width b and the relatively great height of the structures and so strong capillary forces are prevalent. These forces respectively act in the grating gaps 2 on both sides of a grating web 1. Due to the spacings $l_x$ of different length between the filler beams 4, the capillary forces to the left and right of a grating web 1 are not in equilibrium and so said web is bent toward the side of the stronger capillary forces. In this embodiment selected in an exemplary fashion, a total of four bent grating webs 1 are marked by shading. This bending often occurs in the case of grating webs 1 with a length of more than 40 μm and an aspect ratio of more than 50, where the capillary forces become very strong and the mechanical stability of the grating webs 1 no longer suffices.

Such deformed grating structures disrupt the regular arrangement and accordingly are not suitable for use, for example in CT systems for phase-contrast X-ray imaging.

Figure 4:
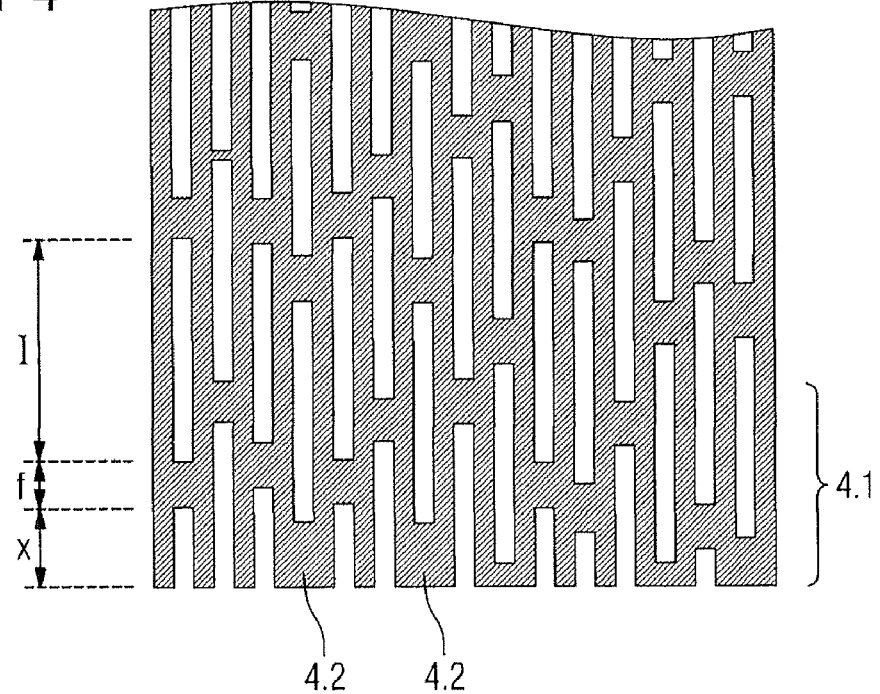
FIG. 4 shows a plan view of a grating with uniformly spaced filler beams.

FIG. 4 shows an embodiment according to the invention of a grating with a large aspect ratio and with a multiplicity of filler beams arranged in the grating gaps. What can be seen here is a much-enlarged plan view. According to an embodiment of the invention, the filler beams are all arranged with a uniform spacing l in the direction of the gaps. Here, the spacing l is limited as a function of the height h of the grating webs and the recurrence p according to the geometric condition $$l = \frac{k}{h} \cdot \left(\frac{p}{2}\right)^3,$$

where k is a constant. This constant limits the spacing l further. It is preferably less than 5000 µm$^{-1}$. Furthermore, it can be limited to the interval between 750 µm$^{-1}$ and 2500 µm$^{-1}$. Uniform beam spacings ensure that the prevalent capillary forces in the grating gaps to the left and right of the grating webs are in equilibrium and the grating webs are accordingly not bent to one side if they have a corresponding length.

In order to prevent the formation of a further grating in the direction perpendicular to the grating gaps, the filler beams are arranged randomly. If, starting from a first side of the grating, a region 4.1 is observed, in which a first filler beam is respectively located in each grating gap, this first filler beam in each case has a spacing x from the first side of the grating. The spacing x in this case lies within the interval (l–5 µm)≧x≧5 µm and can thus vary as a function of the spacing l between adjacent filler beams. In this example embodiment, the first side corresponds to the illustrated lower side of the grating and the first filler beams correspond to the respective lowest filler beams.

Here, the filler beams should not exceed a certain width f in the direction of the gaps so that the effect thereof on the absorption properties of the grating is kept as low as possible. For this, an upper limit of 10% of the beam spacing 1 is suitable, preferably at most 3 µm. Nevertheless, it was found to be expedient to extend the outermost filler beams in a grating gap to the edge of the grating, if the spacing thereof from the edge is less than 5 to 10 µm. Such a short edge region of a grating gap is then completely filled in. Appropriately extended filler beams 4.2 can be seen at the lower side of the grating. The filling of very small edge regions by the extended filler beams 4.2 achieves increased stability of the grating during the production because the grating gaps correspond to a negative impression that, if it is too narrow, can likewise become unstable and so the edge regions are formed in an irregular fashion.

The features of the grating described herein, that is to say (within procedural accuracy) equal spacings between the filler beams with a random arrangement and limitation of the length of the filler beams, have already been used to produce defect-free gratings with a height of up to 60 µm.

FIG. 5 shows a schematic 3D illustration of a focus/detector system of a CT system, with a patient P situated in the beam path as an observation object. The focus F and the detector D are arranged on a gantry (not illustrated in any more detail here) and move around the system axis S in a circular fashion. If, additionally, there is a linear movement of the patient P along the direction of the system axis as the focus/detector system rotates, this results in the spiral scan of the patient P known per se. Three gratings $G_0$, $G_1$ and $G_2$ according to the invention are arranged in the beam path of the focus/detector system, where the first grating $G_0$, which is also referred to as the source grating, is attached in the direct vicinity of the focus F and is penetrated by the X-ray radiation. In the direction of propagation of the X-ray radiation, this is followed by the patient P. In front of the detector D situated on the other side of the system axis S, this is firstly followed by the second grating $G_1$, called the phase grating. Thereafter, this is followed in the radiation direction by the third grating $G_2$, called the analysis grating, which is advantageously arranged directly in front of the detector D. The detector D comprises at least one row with a multiplicity of detector elements. The detector D is preferably designed as a detector with a plurality of rows or as a detector with a multiplicity of rows, wherein said detector is equipped with a multiplicity of detector rows arranged in parallel, each with a multiplicity of detector elements. The connecting lines between the focus F and the individual detector elements during the scan in each case represent an X-ray beam arranged in space, the change in intensity of which is measured by the respective detector element.

Here, the three gratings $G_0$, $G_1$ and $G_2$ have the features according to an embodiment of the invention and have a large aspect ratio. Furthermore, they characterize high mechanical stability and so they are suitable for use in a CT system.

It is understood that the aforementioned features of the invention can be used not only in the respectively specified combination, but also in other combinations or on their own, without departing from the scope of the invention.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A grating with a large aspect ratio, comprising:
a multiplicity of recurring alternating grating webs and grating gaps, each of the respective grating webs including a height; and
a multiplicity of filler beams, respectively arranged in the grating gaps with a spacing from one another in a direction of the gaps, each of the respective filler beams connecting respectively adjacent grating webs over the respective height of the grating webs, wherein the grating webs and the grating gaps run from a first to a second side of the grating, and the filler beams each include a width in a direction of the gaps, the width being at most 10% of the spacing between two adjacent filler beams, and wherein the spacings between respective adjacent ones of the filler beams in each of the grating gaps do not vary by more than 10% in the entire grating.

2. The grating as claimed in claim 1, wherein the spacings between the respective adjacent filler beams in each of the grating gaps are the same in the entire grating within the scope of procedural accuracy.

3. The grating as claimed in claim 1, wherein the spacing (1) between two of the filler beams in one of the grating gaps satisfies the following geometric condition:

$$l = \frac{k}{h} \cdot \left(\frac{p}{2}\right)^3,$$

where k is a constant, h is a height and p is the recurrence of the grating.

4. The grating as claimed in claim 3, wherein the constant k is less than 5000 $\mu m^{-1}$.

5. The grating as claimed in claim 3, wherein the constant k lies in the range between 750 $\mu m^{-1}$ and 2500 $\mu m^{-1}$.

6. The grating as claimed in claim 1, wherein the filler beams are positioned randomly in one of the grating gaps whilst maintaining the separation criterion.

7. The grating as claimed in claim 1, wherein, in each grating gap, there is a first filler beam adjacent to the first side of the grating, wherein the first filler beam includes a spacing (x) from the first side of the grating, the spacing (x) varying within the following geometric conditions:

$$(l-5 \,\mu m) \geqq x \geqq 5 \,\mu m.$$

8. The grating as claimed in claim 1, wherein a width of the filler beams is not more than 3 $\mu m$ in a direction of the gaps.

9. The grating as claimed in claim 1, wherein edge-side filler beams in a grating gap are elongated in a direction of the gaps if the spacing of the edge-side beams from the edge of the grating is smaller than a set value.

10. The grating as claimed in claim 1, wherein, during production of the grating, a primary structure is firstly generated by a lithography method and the grating is produced as a negative impression of the primary structure.

11. The grating as claimed in claim 10, wherein the lithography method is an X-ray lithography method.

12. The grating as claimed in claim 10, wherein the grating is produced by electrodeposition in the primary structure.

13. The grating as claimed in claim 10, wherein the primary structure is generated by a negative photoresist, in particular SU-8.

14. The grating as claimed in claim 1, wherein the grating is arranged on a grating base.

15. The grating as claimed in claim 1, wherein the grating is arranged on a foil.

16. A CT system, comprising at least one grating as claimed in claim 1.

17. The grating as claimed in claim 1, wherein the grating is an X-ray optical grating.

18. The grating as claimed in claim 1, wherein the grating is produced by a lithography method.

19. A CT system, comprising at least one grating as claimed in claim 18.

* * * * *

UNITED STATES PATENT AND TRADEMARK OFFICE
CERTIFICATE OF CORRECTION

PATENT NO. : 8,223,924 B2
APPLICATION NO. : 12/768052
DATED : July 17, 2012
INVENTOR(S) : Martin Börner et al.

Page 1 of 1

It is certified that error appears in the above-identified patent and that said Letters Patent is hereby corrected as shown below:

On the Title Page

Item (73) should read: Assignees: Siemens Aktiengesellschaft, Munich (DE); Karlsruher Institut für Technologie, Karlsruhe (DE)

Signed and Sealed this
Thirteenth Day of November, 2012

David J. Kappos
*Director of the United States Patent and Trademark Office*